United States Patent
Sullivan

(10) Patent No.: US 11,547,583 B2
(45) Date of Patent: Jan. 10, 2023

(54) METHOD AND APPARATUS FOR TREATING CRITICAL LIMB ISCHEMIA

(71) Applicant: Micro Medical Solutions, Inc., Quincy, MA (US)

(72) Inventor: Gregory Sullivan, Quincy, MA (US)

(73) Assignee: Micro Medical Solutions, Inc., Wilmington, MA (US)

( * ) Notice: Subject to any disclaimer, the term of this patent is extended or adjusted under 35 U.S.C. 154(b) by 0 days.

(21) Appl. No.: 15/701,021

(22) Filed: Sep. 11, 2017

(65) Prior Publication Data

US 2018/0071120 A1    Mar. 15, 2018

Related U.S. Application Data

(60) Provisional application No. 62/385,674, filed on Sep. 9, 2016, provisional application No. 62/385,660, filed on Sep. 9, 2016.

(51) Int. Cl.
*A61F 2/90*    (2013.01)

(52) U.S. Cl.
CPC ........ *A61F 2/90* (2013.01); *A61F 2210/0014* (2013.01); *A61F 2230/0069* (2013.01); *A61F 2250/0098* (2013.01)

(58) Field of Classification Search
CPC .............. A61F 2/90; A61F 2250/0098; A61F 2230/0069; A61F 2210/0014
See application file for complete search history.

(56) References Cited

U.S. PATENT DOCUMENTS

| 2002/0010505 A1* | 1/2002 | Richter | A61F 2/915 623/1.34 |
| 2006/0086440 A1* | 4/2006 | Boylan | A61L 31/18 148/563 |
| 2008/0188924 A1* | 8/2008 | Prabhu | A61L 31/16 623/1.16 |
| 2008/0221670 A1* | 9/2008 | Clerc | A61F 2/07 623/1.34 |

(Continued)

FOREIGN PATENT DOCUMENTS

| WO | WO-2013097759 A1 * | 7/2013 | ............... A61F 2/90 |
| WO | WO-2015090237 A1 * | 6/2015 | |

OTHER PUBLICATIONS

Amro, A. et al. (2016). Case Report: Retrograde Tibiopedal Access as a Bail-out Procedure for Endovascular Intervention Complications. Case Reports in Vascular Medicine, 2016(7519748), pp. 1-3.*

(Continued)

*Primary Examiner* — Brian A Dukert
*Assistant Examiner* — Rebecca Lynee Zimmerman
(74) *Attorney, Agent, or Firm* — Bay State IP, LLC

(57) ABSTRACT

A system and method for treating critical limb ischemia (CLI) including a radiopaque micro stent disposed for cross ankle stenting as well as retrograde pedal/tibial artery access, in conjunction with antegrade access for the recanalization of impaired tibial vessels. A radiopaque medical device is constructed from a tubular-shaped body having a thin wall defining a specific strut pattern. In an additional aspect, the present apparatus introduces a new radiopaque medical device, such as a stent, wherein the tubular body includes a super elastic, nickel-titanium (nitinol) alloy.

1 Claim, 3 Drawing Sheets

(56) References Cited

U.S. PATENT DOCUMENTS

| | | | | |
|---|---|---|---|---|
| 2011/0087146 A1* | 4/2011 | Ryan | ............... | A61F 2/04 |
| | | | | 604/8 |
| 2011/0295354 A1* | 12/2011 | Bueche | ............ | A61F 2/966 |
| | | | | 623/1.11 |
| 2013/0226276 A1* | 8/2013 | Newell | ............ | A61F 2/82 |
| | | | | 623/1.11 |
| 2015/0190221 A1* | 7/2015 | Schaefer | ........... | A61F 2/915 |
| | | | | 623/1.11 |
| 2017/0333230 A1* | 11/2017 | Folan | ............. | A61F 2/90 |

OTHER PUBLICATIONS

Manzi, M., et al. (2012). Revascularization of Tibial and Foot Arteries: Below the Knee Angioplasty for Limb Salvage, Angioplasty, Various Techniques and Challenges in Treatment of Congenital and Acquired Vascular Stenoses, Dr. Thomas Forbes (Ed.), ISBN: 978-953-51-0084-3, InTech, Available from: http://www.intech.*
Schaffer, J. (2002). DFT Biocompatible Wire. Advanced Materials & Processes. (Oct. 2002), pp. 51-54.*
EverFlex Informational Sheets (Year: 2012).*
Kawarada, O., et al. (2008). Dorsalis Pedis Artery Stenting for Limb Salvage. Catheterization and Cardiovascular Interventions 71: 976-982 (Year: 2008).*

* cited by examiner

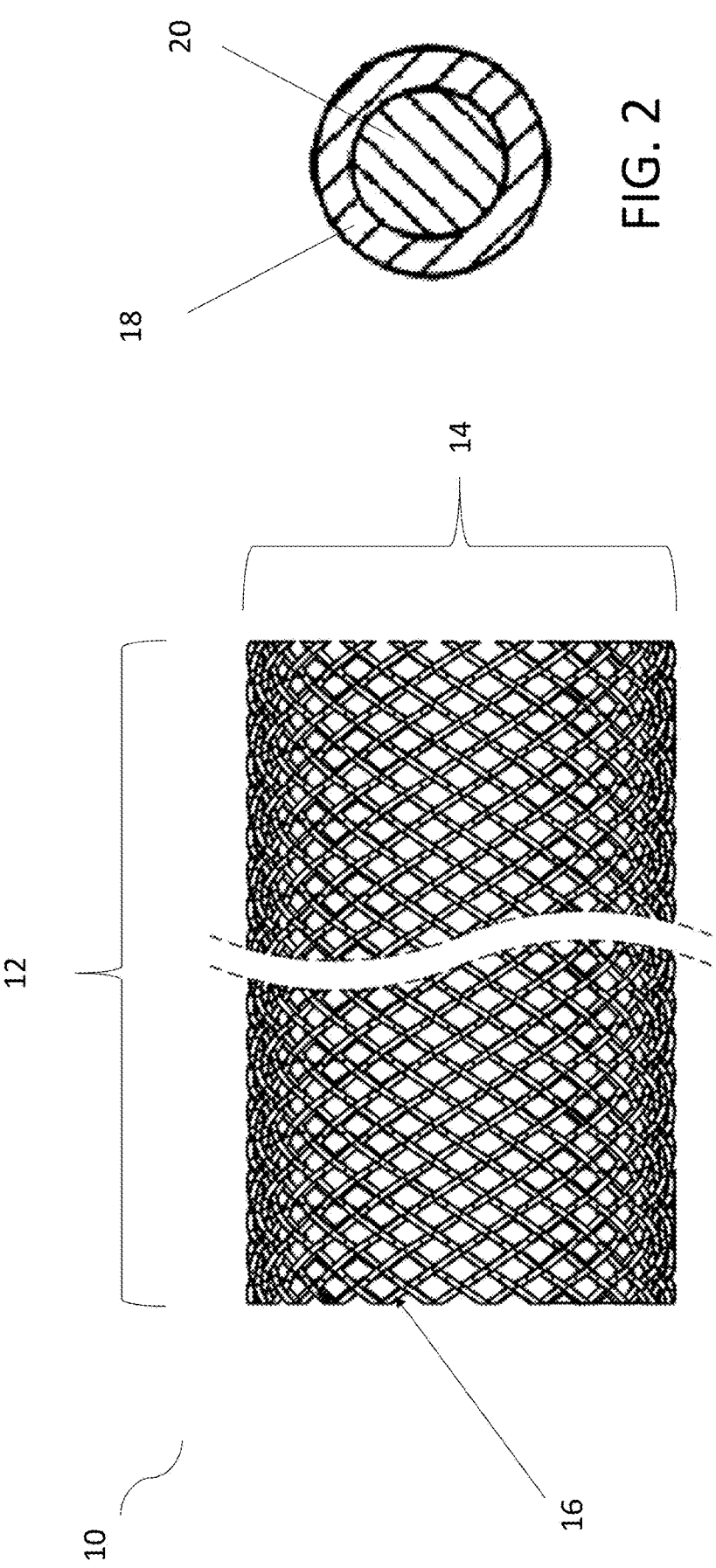

FIG. 4

- 100 — utilizing a radiopaque micro stent
- 110 — utilizing below-the-knee revascularization method by entering the body of the patient in a region below the knee
- 120 — Entering the body through a pedal access point
- 130 — Utilizing an ultrasound machine in conjunction with the radiopaque micro stent for guidance and delivery of the radiopaque micro stent
- 140 — Proceeding retrograde through a tibial artery to deliver the radiopaque micro stent
- 150 — Delivering and seating the stent via an image from the ultrasound machine
- 160 — Unblocking tibial artery occlusions

METHOD AND APPARATUS FOR TREATING CRITICAL LIMB ISCHEMIA

CROSS-REFERENCE TO RELATED APPLICATIONS

This application claims the benefit of and takes priority from U.S. Provisional Application No. 62/385,660 filed on Sep. 9, 2016, and U.S. Provisional Application No. 62/385,674, filed on Sep. 9, 2016, the contents of which are hereby incorporated by reference.

BACKGROUND OF THE INVENTION

Field of the Invention

The present invention pertains to medical devices and methods and more particularly a critical limb ischemia CLI therapy methods that allows for below the ankle stenting with specifically designed devices and detection methods.

Description of the Related Art

Stents are typically implanted in a body lumen, such as carotid arteries, coronary arteries, peripheral arteries, veins, or other vessels to maintain the patency of the lumen. These devices are frequently used in the treatment of atherosclerotic stenosis in blood vessels especially after percutaneous transluminal angioplasty (PTA) or percutaneous transluminal coronary angioplasty (PTCA) procedures with the intent to reduce the likelihood of restenosis of a vessel. Stents are also used to support a body lumen, tack-up a flap or dissection in a vessel, or in general where the lumen is weak to add support.

Within the art, currently disposed stent devices include, but are not limited to, elongated devices used in many capacities, including but not limited to support an intraluminal wall. Stenosis is an abnormal narrowing in a blood vessel or other tubular organ or structure. This vessel narrowing prevents the valve from opening fully, which obstructs blood flow from the heart and onward to the rest of the body.

There concurrently exist a wide variety of stents used for different purposes depending on the type of narrowing of a vessel in the body required. As used herein, the term "stent" is a shorthand reference referring to the wide varieties of stents, both covered and uncovered.

Stents are typically implanted within the vascular system to reinforce collapsing, partially occluded, weakened or under dilated sections of vessel and valves. Stents have also been successfully implanted in urinary tracts and bile ducts to reinforce those body vessels. This invention is applicable in all of these situations.

In general, the typical procedure for implanting self-expanding stent is to first open the region of the vessel with a balloon catheter and then place the stent in a position bridging the weakened portion of the vessel. Positioning of the stent may be followed by the technique known as the "Swiss Kiss" in which a separate balloon catheter is positioned within the stent and expanded to radially expand the stent for implantation.

Stents are often times implanted in vessels that are closer to the surface of the body, such as in the carotid arteries in the neck or in peripheral arteries and veins in the leg. Because these stents are so close to the surface of the body, they are particularly vulnerable to impact forces that can partially or completely collapse the stent and thereby block fluid flow in the vessel. Other forces can impact balloon expandable stents and cause similar partial or total vessel blockage. A collapse obstructs the lumen and restricts blood flow in the vessel in which they are implanted.

Since balloon expandable stents are plastically deformed, once collapsed or crushed they remain so, permanently blocking the vessel. Thus, balloon expandable stents under certain conditions might pose an undesirable condition for the patient.

Self-expanding stents as the name implies self-expand through the properties of the material constituting the stent. The inflation force of a balloon catheter is usually not necessary to deploy this kind of stent.

Further to counter any inflexibility, stents may be made from flexible material. Clearly, self-expanding, nickel-titanium stents are useful and valuable to the medical field. But a distinct disadvantage with self-expanding nickel-titanium stents is the fact that they are not sufficiently radiopaque as compared to a comparable structure made from gold or tantalum.

Radiopacity permits the cardiologist or physician to visualize the procedure involving the stent through use of fluoroscopes or similar radiological equipment. Good radiopacity is therefore a useful feature for self-expanding nickel-titanium stents to have.

Some stents are covered with a radiopaque coating. Radiopacity can be improved through coating processes such as sputtering, plating, or co-drawing gold or similar heavy metals onto the stent. These processes, however, create complications such as material compatibility, galvanic corrosion, high manufacturing cost, coating adhesion or delamination, biocompatibility, loss of coating integrity following collapse and deployment of the stent, etc. This has the advantage, that the stent can clearly be viewed. On the other hand, the metallic stent plated with a radiopaque metal has the disadvantage that, if the boundary surface between the two materials comes into contact with blood or another water-containing fluid the stent may be corrupted by electrolytic corrosion. Furthermore, the coating of the stent with materials like gold is relatively expensive.

Another possible solution is to attach a portion containing the radiopaque material to the web structure. In this case, there is an area where the two materials are in contact together. Normally, both materials are made of metal. If blood flowing through the vessel comes into contact with the two different metals, electrolytic corrosion will occur which will lead to a damage of the stent and/or to an irritation of the vessel.

Concurrently, there are several types of radiopaque stents that exist for different applications and procedures. Materials that inhibit the passage of electromagnetic radiation are called radiodense or radiopaque, while those that allow radiation to pass more freely are referred to as radiolucent. The term refers to the relatively white appearance of dense materials or substances on imaging studies, compared with the relatively darker appearance of less dense materials. Heavy metals, such as lead, cobalt and chromium, are considered radiopaque. Other radiopacifiers include barium sulfate, bismuth, and tungsten. Many stents utilize radiopaque materials in one way or another in order to allow the medical staff to see the stent on an x-ray (after insertion) or fluoroscopy (during insertion).

One issue faced with incorporating heavy metals into a stent is avoiding the heavy metal coming into contact with live tissue in the body. Numerous systems concurrently incorporate radiopaque materials into a stent utilizing various methods and devices. Some of these include radiopaque coatings, radiopaque cores, and even radiopaque rivets or welds. Further, some systems may utilize radiopaque markers may be placed anywhere along a stent, intermittently throughout the stent or on the ends of the stent.

SUMMARY OF THE INVENTION

The instant series of system, method and series of apparatuses, as illustrated herein, are clearly not anticipated, rendered obvious, or even present in any of the prior art mechanisms, either alone or in any combination thereof. Thus, the several embodiments of the instant system are illustrated herein.

In one aspect, the present apparatus introduces a manner in which to remove atherosclerosis from blood vessels and recanalize arteries, through intervention below the knee of the patient.

It is an object of the instant system to introduce a radiopaque medical device, such as a stent, for use or implementation in a body lumen. In a preferred embodiment, the stent may be used in patients with critical limb ischemia (CLI), below-the-knee revascularization.

It is an additional object of the instant system to introduce an interruptive concept of stenting at the level of the ankle strap area, which includes an extension of a stent from above the ankle to below the ankle, including the pedal circulation.

It is an object of the instant system to introduce a radiopaque medical device which vitiates ankle strap crush effect and overcomes areas of high stress, torsion, extension, and body weight considerations, in below the ankle procedures.

In recent years, for the treatment of critical limb ischemia, many medical professionals have investigated employment of a method know as endovascular intervention. Like any evolving treatment, utilization of endovascular intervention poses multiple challenges including issues with lesions formed from occlusions, or blockage in a canal, vessel, or passage of the body. Retrograde pedal/tibial artery access, in conjunction with antegrade access proves to recanalize impaired tibial vessels.

In an additional preferred embodiment, a radiopaque medical device is constructed from a tubular-shaped body having a thin wall defining a specific strut pattern. In an additional aspect, the present apparatus introduces a new radiopaque medical device, such as a stent, wherein the tubular body includes a super elastic, nickel-titanium (nitinol) alloy.

In one embodiment, the alloy may further include an additional element of platinum. In an additional embodiment, the alloy may further include an additional element selected from the group of chemical elements consisting of iridium, gold, tungsten, rhodium, tantalum, silver, etc.

In one aspect the present apparatus introduces a new radiopaque medical device, such as a stent, wherein the stent is highly radiopaque.

In a further aspect, the present apparatus introduces a new radiopaque medical device, such as a stent, wherein the stent does not require multiple layers or coatings of both nitinol and a radiopaque material. Rather, the radiopaque device, such as a stent, wherein the body of the stent comprises one alloy of combined nitinol and radiopaque material such as platinum.

In another aspect, the present apparatus introduces a new radiopaque medical device, such as a stent, wherein the stent is self-expanding. The self-expanding stent may be loaded within a delivery system. When loaded, the stent if collapsed and then released at a point of delivery. Herein, the stent may be designed to perform various mechanical function within a lumen. In a preferred embodiment, the radiopaque, self-expanding stent may be used in patients with critical limb ischemia (CLI), below-the-knee revascularization. Because the preferred embodiment is to utilize the stent in patients with critical limb ischemia, it is an additional embodiment that the additional element alloyed with the nitinol does not diminish the super elastic characteristics of a nitinol stent.

To achieve sufficient degree of radiopacity and still ensure that the super elastic properties of the stent stay true, in one aspect, the present apparatus, includes a stent wherein the platinum additional element's atomic percent is greater than or equal to 2.5 and less than or equal to 15. With these characteristics, the platinum still comprises high radiopacity but does not inhibit the flexibility and elastic qualities of the nitinol.

In yet another aspect, the present invention introduces a method for providing a radiopaque nitinol-platinum stent. In a preferred embodiment, the method entails providing a tubular-shaped body having a thin wall, wherein the body includes a super elastic nitinol alloy and the alloy further includes an additional element such as platinum. In further embodiments, the additional element may also be selected from the group of chemical elements consisting of iridium, gold, rhenium, tungsten, palladium, rhodium, tantalum, silver, ruthenium, or hafnium. The method further includes forming a strut pattern; wherein the stent is highly radiopaque. The step of providing a tubular-shaped body includes melting nickel, titanium, and the ternary element and cooling the mixture to form an alloy ingot, hot forming the alloy ingot, hot or cold forming the alloy ingot into a cylinder, drilling the cylinder to form tubing, cold drawing the tubing, and annealing the tubing.

Realizing one aspect of the present invention relates to a new medical device, such as a stent, that is biocompatible, radiopaque and MRI compatible. In another preferred embodiment, a radiopaque and MRI compatible medical device, such as a stent, is constructed from a tubular-shaped body having a thin wall defining a strut pattern; wherein the tubular body includes a nitinol alloy, and the alloy further includes a the additional element of platinum. A preferred embodiment would include nickel and titanium plus either platinum.

The alloy having a composition of the present invention can be used with any medical device, especially medical devices that require either radiopacity or MRI compatibility. In some embodiments, these ternary elements depress the transformation temperature such that no stress induced martensite is formed at body temperature.

In one embodiment, a braided woven stent in the body utilizing a combination of nitinol tube w/a small core of platinum for both for deployment/delivery purposes in the body and diagnostic applications. Stent has been designed specifically for usage in procedures below the knee, i.e. for the anterior tibial, posterior tibial, and peroneal arteries of the lower leg. We are also targeting the pedal artery that runs in the foot but we have not conducted the testing as of yet.

In one embodiment, the stent will be used in conjunction with balloon angioplasty and/or other interventional procedures such as atherectomy. Atherectomy is a minimally invasive endovascular surgery technique for removing atherosclerosis from blood vessels within the body. It is an alternative to angioplasty for the treatment of peripheral artery disease, with no evidence of superiority to angioplasty. The stent will be deployed after these procedures to provide a scaffold to maintain stent patency. With the scaffold in place, restoration of blood flood could avoid the need for amputation.

The utilization of platinum increases visualization of the stent both during deployment and post procedural. Thus, platinum primarily is used for enhancement under fluoroscopy but is also highly visible by way of ultrasound. The use of ultrasound could ultimately move the procedure from the catheterization laboratory or cath lab to a physician's office.

In terms of deployment and use in the body, in one embodiment, the stent is utilized to enter the body below the knee and then wrap around the ankle while using ultrasound for detection and positioning, a pedal/tibial access (at the ankle) and proceeding retrograde to deploy the stent in the lower leg. Regarding deployment of the stent in the foot, the same access point may be utilized, however, the physician would proceed antegrade.

In many scenarios, the retrograde approach, especially when entering sufficiently close to the occlusion, allows for successful crossing of the occlusion, with a very low rate of occlusion at the access point of the pedal/tibial vessel. Accessing the pedal/tibial vessels in retrograde fashion is normally more successful than the antegrade approach, however, with the additional usage of an ultrasound assist with the instant radiopaque system, a much greater success rate in getting the apparatus through the occlusion may be exhibited within antegrade scenarios.

In one embodiment, fluoroscopy may be utilized in order to assist the administering physician. Fluoroscopy is a type of medical imaging that shows a continuous medical X-ray image on a monitor, much like an X-ray movie, to obtain real-time moving images of the interior of an object. During a fluoroscopy procedure, an X-ray beam is passed through the body allowing a physician to observe the internal structure and function of a patient, in others words both the anatomy and physiology of a patient.

In another embodiment, ultrasound may be utilized in order to assist the administering physician. Ultrasound may be defined as frequencies higher than the upper audible limit of humans earing range. Ultrasound is no different from 'normal' (audible) sound in its physical properties, except in that humans cannot hear it. This limit varies from person to person and is approximately 20 kHz (20,000 hertz) in healthy, young adults. Ultrasound devices operate with frequencies from 20 kHz up to several gigahertz. Ultrasound is used in many different fields. Ultrasonic devices are used to detect objects and measure distances. Ultrasound imagining or sonography is often used in medicine. Medical sonography (ultrasonography) is an ultrasound-based diagnostic technique used to visualize muscles, tendons, and many internal organs, to capture their size, structure and any pathological lesions with real time tomographic images.

There has thus been outlined, rather broadly, the more important features of a medical device delivery system for protection during surgery embodiments in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

These together with other objects of the invention, along with the various features of novelty, which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

Advantages of the present invention and better understanding will be apparent from the following detailed description of exemplary embodiments thereof, which description should be considered in conjunction with the accompanying drawings, in which:

FIG. 1 is a simple cross-sectional view shown lengthwise of a braided non-woven micro stent in accordance with one embodiment of the present system.

FIG. 2 is a cross-sectional view of an individual strand of the braided non-woven micro stent.

FIG. 4 illustrates a flow diagram for treating critical limb ischemia utilizing the micro stent for insertion below the knee or through the ankle.

DETAILED DESCRIPTION OF THE SEVERAL EMBODIMENTS

Figure 3B:
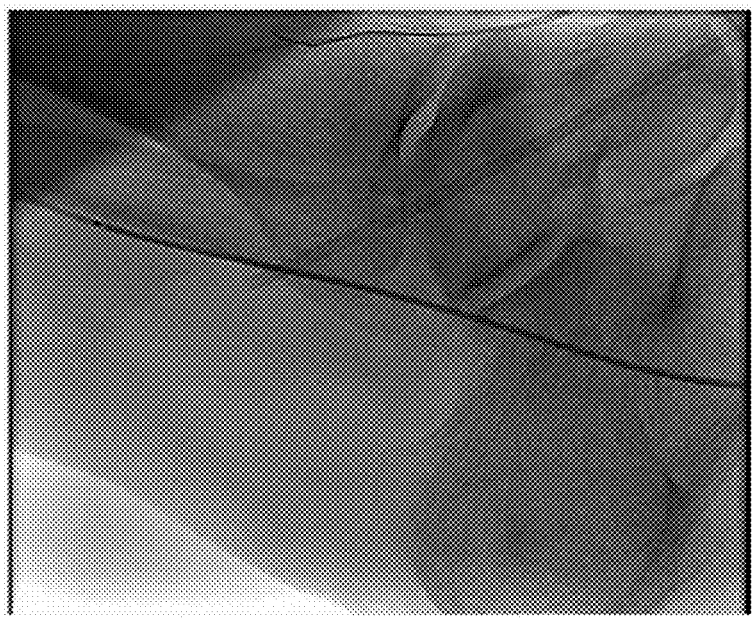
FIGS. 3A-3B shows the micro stent into the Left Popliteal sheath and detected under ultrasound.

Embodiments of the present series of apparatuses, systems and interrelated methods pertain to a coil-reinforced stent use during angioplasty procedures. Throughout the description, for the purposes of explanation, numerous specific details are set forth in order to provide a thorough understanding of the present invention. It will be apparent, however, to one skilled in the art that the present invention may be practiced without some of these specific details. In other instances, well-known structures and devices are shown in generic form to avoid obscuring the underlying principles of the present invention.

FIG. 1 illustrates a cross-section view of one embodiment of a braided non-woven micro stent 10, wherein the micro stent 10 is preferably comprises of forty-eight (48) individual strands arranged in a braided configuration for use in a patient during a medical procedure. In the embodiment shown, the micro stent 10 possesses a length 12 and an outer diameter 14 that defines the overall size of the micro stent 10. Each individual strand 16 of the micro stent 10 is preferably comprised of an outer layer 18 and an inner layer 20 (see FIG. 2).

The actual dimensions of the micro stent 10 may vary depending on the specific medical procedure and/or patient, however the micro stent 10 may be configured as follows:

| Labeled Size | Outer Diameter | Length |
|---|---|---|
| 3.0 mm × 40 mm | 3.4 mm | 40 mm |
| 3.0 mm × 60 mm | 3.4 mm | 60 mm |
| 3.5 mm × 40 mm | 4.0 mm | 40 mm |
| 3.5 mm × 60 mm | 4.0 mm | 60 mm |
| 4.0 mm × 40 mm | 4.6 mm | 40 mm |

| Labeled Size | Outer Diameter | Length |
| --- | --- | --- |
| 4.0 mm × 60 mm | 4.6 mm | 60 mm |
| 4.5 mm × 40 mm | 5.2 mm | 40 mm |
| 4.5 mm × 60 mm | 5.2 mm | 60 mm |

FIG. 2 illustrates a cross-sectional view of an individual strand 16 of the micro stent 10 comprising an outer layer 18 and an inner layer 20. In one embodiment, the outer layer 18 is comprised of platinum and the inner layer 20 is comprised of nitinol.

Figure 3A:
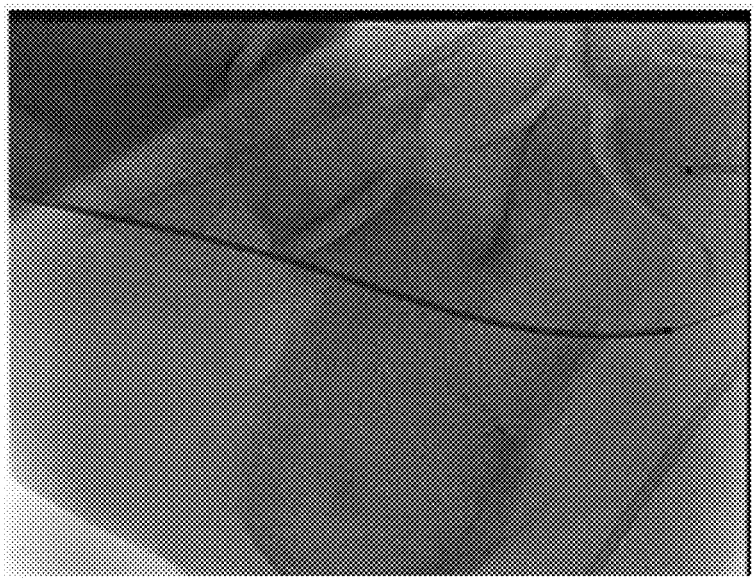

FIGS. 3A-3B illustrates various depictions of the micro stent 10 being deployed and detected via ultrasound. FIG. 4 illustrates a flow diagram for treating critical limb ischemia utilizing the micro stent for insertion below the knee or through the ankle.

FIG. 4 illustrates a method for treating critical limb ischemia utilizing the micro stent 10, wherein at step 100, a radiopaque micro stent is utilized. Next at step 110, utilizing below-the-knee revascularization method by entering the body of the patient in a region below the knee; and then entering the body through a pedal access point at step 120. Subsequently at step 130, utilizing an ultrasound machine in conjunction with the radiopaque micro stent for guidance and delivery of the radiopaque micro stent, followed by at step 140 in proceeding retrograde through a tibial artery to deliver the radiopaque micro stent. Lastly at step 150, delivering and seating the stent via an image from the ultrasound machine and then at step 160, unblocking tibial artery occlusions.

The method of treating critical limb ischemia (CLI) may further comprising the steps of: reutilizing the pedal access point; proceeding antegrade around the ankle to reach legions and occlusions on the opposing side of the pedal access point; and utilizing a continuous medical X-ray image for positioning and guidance.

In an additional embodiment, the micro stent may comprise a Nitinol and Platinum composite comprising 90 percent Nitinol and 10 percent Platinum; and a structure comprising forty eight strands.

In one embodiment, a medical device for use in a body lumen, comprising a braided composite of DFT® wires, comprising tubular-shaped body having a wall defining a pattern of struts, wherein the tubular-shaped body comprises a nickel-titanium alloy, said nickel-titanium alloy further comprising at least one additional element platinum.

In additional embodiments, the medical device of claim 1, wherein the tubular-shaped body is a radiopaque stent. The medical device of claim wherein the device is radiopaque and comprises nitinol and additional element that may be chosen from the group consisting of iridium, platinum, rhenium, palladium, rhodium, silver, ruthenium, osmium, zirconium, and molybdenum.

The micro stent is manufactured by utilizing individual strands of NiTi #1 DFT®-10% Platinum composition (Fort Wayne Metals) and braiding the wire into a stent in the body. When the wire is braided on a mandrel is then heat set and quenched forming the wires into the cylindrical configuration. The stent then undergoes a process to remove the oxide formed during heat treating.

In a preferred embodiment, forty eight (48) strands NiTi #1 DFT®-10% Pt composition may be utilized. Although many rations of platinum to nitinol may be employed, including a of 5% to 50%, utilization of 10% Platinum to Nitinol ration represents an optimum compromise between visualization and mechanical performance as every increase in platinum, the wire becomes more visible but the material properties diminish, it becomes weaker and less flexible. In a further embodiment, Silk® NiTi (Fort Wayne Metals) may be utilized.

In one embodiment, the micro stent may be employed in conjunction with a 3 French (Fr) compatible balloon (micro balloon) that can be placed under ultrasound as an outpatient procedure. This would allow the physician to dilate a de novo lesion or restenotic lesion in Rutherford 5 patients for therapy for CLI. The micro balloon's low profile, visibility under ultrasound, and high pressure capabilities will allow the physician to perform a staged therapy in the outpatient setting under ultrasound guidance.

The micro stent, self-expanding stent, is disposed to be deployed from the lateral plantar to the distal PT and thus possess the capability to extend across the across the ankle joint. Thus the micro stent brings into play a stent which can sustain high filling pressure to the microcirculation for better and faster wound healing.

The stent design allows for side branches to stay patent and what generally occurs once you put a stent across a side branch is that you see the ostum of that side branch get pinched. We know from experience that when we go back, that side branch either ends up with a trickle of flow or thrombus present. The phenomenon I see with this stent design is that you can put it across side branches and the side branches are flowing and filling. This would be welcome news for CLI patients.

As CLI patients do not normally tolerate the viscosity of contrast and often have underlying renal issues, having the ability to treat patients comfortably with ultrasound guidance via a pedal approach in an outpatient setting is now a reality

What is claimed:

1. A method of treating critical limb ischemia (CLI) comprising the steps of:
    utilizing a self-expanding radiopaque stent constructed from a tubular-shaped body having a wall defining a specific strut pattern and configured for usage in procedures below the knee and the ankle strap area, wherein the self-expanding radiopaque stent is configured to expand across the ankle joint from above the ankle to below the ankle;
    utilizing a below-the-knee revascularization method to a body of a patient;
    entering the body with the self-expanding radiopaque stent through a pedal access point below the knee or at the ankle;
    delivering the self-expanding radiopaque stent from the lateral plantar to the distal posterior tibial;
    utilizing an ultrasound machine to assist in the delivery of the self-expanding radiopaque stent;
    utilizing a continuous medical X-ray image to provide real-time monitoring of the positioning of the self-expanding radiopaque stent;
    delivering and seating the self-expanding radiopaque stent via an image from the ultrasound machine;
    unblocking tibial artery occlusions;
    reutilizing the pedal access point below the knee or at the ankle; and
    proceeding antegrade around the ankle or retrograde in below-the-knee area to reach lesions and occlusions on an opposing side of the pedal access point.

* * * * *